(12) United States Patent
Phelps et al.

(10) Patent No.: US 6,576,739 B2
(45) Date of Patent: Jun. 10, 2003

(54) METHOD OF POLYCARBONATE PREPARATION

(75) Inventors: Peter David Phelps, Schenectady; Elliott West Shanklin, Altamont; Daniel Joseph Brunelle, Burnt Hills, all of NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/735,871

(22) Filed: Dec. 14, 2000

(65) Prior Publication Data

US 2002/0111456 A1 Aug. 15, 2002

Related U.S. Application Data

(60) Provisional application No. 60/202,706, filed on May 10, 2000.

(51) Int. Cl.[7] .................................................. C08G 64/00
(52) U.S. Cl. ....................... 528/196; 528/198; 528/202
(58) Field of Search ................................ 528/196, 198, 528/202

(56) References Cited

U.S. PATENT DOCUMENTS

| 3,193,529 A | 7/1965 | Oxenrider |
| 4,316,980 A | 2/1982 | Idel et al. |
| 4,368,315 A | 1/1983 | Sikdar |
| 4,471,105 A | 9/1984 | Campbell et al. |
| 5,212,281 A | 5/1993 | Munjal et al. ............... 528/202 |
| 5,288,837 A | 2/1994 | Munjal et al. |
| 5,739,257 A | 4/1998 | Boden et al. ............... 528/196 |

FOREIGN PATENT DOCUMENTS

| DE | 2315888 | 10/1974 |
| EP | 0004021 | 9/1979 |
| GB | 808490 | 3/1957 |
| GB | 841654 | 3/1958 |

OTHER PUBLICATIONS

"The Interfacial Polycondensation of Tetrabromobisphenol-A Polycarbonate.\I. Model Reaction and Mechanism Studies", Angewandte Makromolekulare Chemie. Applied Macromolecular Chemistry and Physics, Wiley Vch, Weinheim, DE, vol. 208, May 1, 1993, pp. 65–77, XP000372853.

*Primary Examiner*—Terressa M. Boykin
(74) *Attorney, Agent, or Firm*—Andrew J. Caruso; Noreen C. Johnson

(57) ABSTRACT

High molecular weight polycarbonates are prepared from hindered bisphenols in a reaction sequence involving conversion of the hindered bisphenol to the corresponding bischloroformate and subsequent treatment with an amine catalyst and aqueous base to effect polymerization by hydrolysis and condensation of the bischloroformate groups. Tertiary aliphatic and cycloaliphatic amine catalysts bearing at least one methyl group are found to be especially effective in promoting this polymerization reaction. Reaction rates and selectivities are shown to be superior to known methods employing tertiary amines lacking methyl groups attached to nitrogen, such as triethylamine. The inclusion of chain stoppers allows the preparation of well defined mixtures of polycarbonate oligomers from hindered bisphenols. Additionally, the methodology may be used to prepare symmetrical diaryl carbonates from hindered phenols.

44 Claims, No Drawings

METHOD OF POLYCARBONATE PREPARATION

RELATED APPLICATIONS

This application claims the benefit of U.S. Provisional Application No. 60/202,706, filed May 10, 2000 the contents of which are hereby incorporated by reference.

BACKGROUND OF THE INVENTION

This invention relates to a general method of polycarbonate preparation applicable to the manufacture of polycarbonates from sterically hindered bisphenols and provides a means for preparing either high molecular weight polycarbonates or low molecular weight polycarbonate oligomers. In addition, the method further relates to a method of making symmetrical diaryl carbonates from sterically hindered phenols.

The preparation of polycarbonates via interfacial polymerization of a bisphenol upon treatment with phosgene is practiced commercially on a world wide basis. The major polycarbonate so produced is that prepared from bisphenol A. Polycarbonate is obtained upon treatment a mixture of bisphenol A in a water immiscible solvent, such as methylene chloride, with a slight excess of phosgene in the presence of an amine catalyst, such as triethylamine, and sufficient aqueous sodium hydroxide to complete the conversion of essentially all of the intermediate chloroformate groups to carbonate groups. Bisphenol A polycarbonate possesses many outstanding properties such as transparency, high impact strength and excellent molding properties but lacks many of the attributes of polycarbonates prepared from bisphenols more sterically hindered than bisphenol A. Such attributes include the high glass transition temperature and hydrolytic stability of polycarbonate prepared from 2,2-bis (3,5-dimethyl-4-hydroxyphenyl)propane (TMBPA), and the flame retardancy of polycarbonate prepared from bis(3,5-dibromo-4-hydroxyphenyl)propane (TBBPA). The hydroxyl groups of Bisphenol A are relatively unhindered and as a consequence bisphenol A reacts readily under interfacial conditions to form polycarbonate without recourse to the use of a large excess of phosgene. The importance of steric hindrance becomes apparent in situations in which the preparation of a polycarbonate from a bisphenol having sterically hindered hydroxyl groups is attempted. Thus, sterically hindered bisphenols such as TMBPA or TBBPA afford only very low molecular weight materials when subjected to interfacial polymerization conditions which successfully convert bisphenol A into high molecular weight polycarbonate. Higher molecular weight polycarbonates may be obtained from sterically hindered bisphenols through the use of interfacial polymerization conditions which employ a large excess of phosgene and long reaction times, but molecular weights of the product polymers are still limited with respect to molecular weights attainable in the interfacial polymerization reaction of bisphenol A and phosgene.

There exists a need for methods to effect the preparation of polycarbonates from sterically hindered bisphenols wherein the molecular weight of the product polycarbonate may be controlled to produce either high or low molecular weight materials and in which method the use of excess phosgene and long reaction times is minimized.

BRIEF SUMMARY OF THE INVENTION

In one aspect the present invention relates to a process for making a polycarbonate comprising structural units I

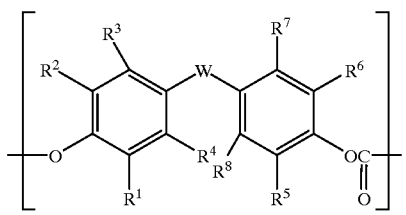

wherein $R^1$–$R^8$ are independently hydrogen, halogen, $C_1$-$C_{20}$ alkyl, $C_6$-$C_{20}$ aryl, $C_7$-$C_{21}$ aralkyl or $C_5$-$C_{20}$ cycloalkyl;

W is a bond, an oxygen atom, a sulfur atom, a $SO_2$ group, a $C_6$–$C_{20}$ aromatic radical, a $C_6$–$C_{20}$ cycloaliphatic radical or the group

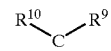

wherein $R^9$ and $R^{10}$ are independently hydrogen, $C_1$-$C_{20}$ alkyl, $C_6$-$C_{20}$ aryl, $C_7$-$C_{21}$ aralkyl or $C_5$-$C_{20}$ cycloalkyl, or $R^9$ and $R^{10}$ together form a $C_4$-$C_{20}$ cycloaliphatic ring which is optionally substituted by one or more $C_1$-$C_{20}$ alkyl, $C_6$-$C_{20}$ aryl, $C_5$-$C_{21}$, aralkyl, $C_5$-$C_{20}$ cycloalkyl groups or a combination thereof;

said method comprising:

(A) admixing a solvent, water, optionally one or more phase transfer catalysts and optionally one or more chain stoppers, with at least one bisphenol having structure II

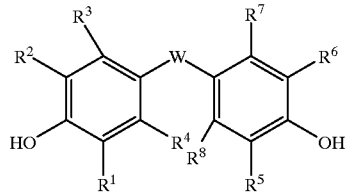

(B) adding phosgene and sufficient aqueous base to maintain a pH in a range between about 5 and about 14; said phosgene being added incrementally in an amount equivalent to between about 1.01 and about 1.75 equivalents based upon the amount of bisphenol used in step (A);

(C) adding a catalyst in an amount corresponding to between about 0.001 and about 0.10 equivalents based upon the amount of bisphenol used in step (A), said catalyst having structure III

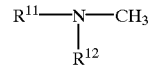

wherein each $R^{11}$ and $R^{12}$ is independently a $C_1$–$C_{18}$ alkyl group, a $C_3$–$C_{18}$ cycloalkyl group, or $R^{11}$ and $R^{12}$ together form a $C_4$-$C_{20}$ cycloaliphatic ring which may be substituted by one or more $C_1$-$C_{20}$ alkyl, $C_6$-$C_{20}$ aryl, $C_5$-$C_{21}$ aralkyl, $C_5$-$C_{20}$ cycloalkyl groups or a combination thereof; and (D) agitating the mixture formed by steps (A), (B) and (C) at a pH in a range between about 8 and about 14 until said mixture is free of chloroformate groups.

Another aspect of the present invention relates to high and low molecular weight polycarbonates formed from sterically hindered bisphenols. The invention further relates to articles formed from said polycarbonates. The present invention further relates to the preparation of symmetrical diaryl carbonates of sterically hindered phenols.

DETAILED DESCRIPTION OF THE INVENTION

The present invention may be understood more readily by reference to the following detailed description of preferred embodiments of the invention and the examples included herein. In this specification and in the claims which follow, reference will be made to a number of terms which shall be defined to have the following meanings.

"BPA" is herein defined as bisphenol A and is also known as 2,2-bis(4-hydroxyphenyl)propane, 4,4'-isopropylidenediphenol and p,p-BPA.

"Mesitol" is herein defined as 2,4,6-trimethylphenol.

As used herein the term "aromatic radical" refers to a radical having a valence of at least one comprising at least one aromatic group. Examples of aromatic radicals include phenyl, pyridyl, furanyl, thienyl, naphthyl, phenylene, biphenyl. The term includes groups containing both aromatic and aliphatic components, for example a benzyl group.

As used herein the term "aliphatic radical" refers to a radical having a valence of at least one comprising a linear or branched array of atoms which is not cyclic. The array may include heteroatoms such as nitrogen, sulfur and oxygen or may be composed exclusively of carbon and hydrogen. Examples of aliphatic radicals include methyl, methylene, ethyl, ethylene, hexyl, hexamethylene and the like.

As used herein the term "cycloaliphatic radical" refers to a radical having a valance of at least one comprising an array of atoms which is cyclic but which is not aromatic. The array may include heteroatoms such as nitrogen, sulfur and oxygen or may be composed exclusively of carbon and hydrogen. Examples of cycloaliphatic radicals include cyclcopropyl, cyclopentyl cyclohexyl, tetrahydrofuranyl and the like.

As used herein the term "solvent" refers to a single pure solvent such as methylene chloride, or in the alternative to mixtures of solvents such as a mixture of methylene chloride and toluene.

In one aspect the instant invention provides a method for the preparation of both high and low molecular weight polycarbonates incorporating repeat units I via interfacial polymerization of bisphenols II with phosgene. In some instances, a mixture of bisphenols is interfacially polymerized to afford a copolycarbonate which may include repeat units I derived from one or more hindered phenols, such as 2,2-bis(3,5-dibromo-4-hydroxyphenyl)propane, as well as repeat units I derived from relatively unhindered bisphenols, such as 2,2-bis(4-hydroxyphenyl)propane.

Accordingly, in step (A) at least one bisphenol II is combined with a water immiscible solvent, water and optionally a chain stopper, and optionally a phase transfer catalyst. Prior to the introduction of phosgene, sufficient aqueous base is added to raise the pH of the reaction mixture to a range between about 9 and about 14, preferably between about 11 and about 13.5. In step (B) the mixture is stirred and about 1.01 to about 1.75 equivalents, preferably about 1.01 to about 1.30 equivalents and still more preferably about 1.01 to about 1.20 equivalents of phosgene is introduced into the reaction mixture together with sufficient aqueous base to maintain the pH in a range between about 9 and about 14, preferably between about 10 and about 13.5. In step (C) an amine catalyst having structure III is added in an amount corresponding to between about 0.1 and about 10, preferably about 0.1 and about 5, and still more preferably about 0.1 and about 1 mole percent based upon the total number of moles of bisphenol employed. In step (D) sufficient aqueous base is added to the reaction mixture to maintain a pH in a range between about 8 and about 14, preferably about 9 and about 13, and the mixture is stirred until chloroformate groups are no longer detectable in the mixture. In one embodiment the present invention is a process for preparing polycarbonates from sterically hindered bisphenols II in which the order of the steps is (A), then (B), then (C) and then (D). In another embodiment of the present invention step (C) precedes step (B) as in the process wherein step (A) is followed by, step (C), which is followed by step (B), which is followed by step (D).

Suitable bisphenols II are illustrated by, but are not limited to 2,2-bis(4-hydroxyphenyl)propane (bisphenol A); 2,2-bis(3-chloro-4-hydroxyphenyl)propane; 2,2-bis(3-bromo-4-hydroxyphenyl)propane; 2,2-bis(4-hydroxy-3-methylphenyl)propane; 2,2-bis(4-hydroxy-3-isopropylphenyl)propane; 2,2-bis(3-t-butyl-4-hydroxyphenyl)propane; 2,2-bis(3-phenyl-4-hydroxyphenyl)propane; 2,2-bis(3,5-dichloro-4-hydroxyphenyl)propane; 2,2-bis(3,5-dibromo-4-hydroxyphenyl)propane; 2,2-bis(3,5-dimethyl-4-hydroxyphenyl)propane; 2,2-bis(3-chloro-4-hydroxy-5-methylphenyl)propane; 2,2-bis(3-bromo-4-hydroxy-5-methylphenyl)propane; 2,2-bis(3-chloro-4-hydroxy-5-isopropylphenyl)propane; 2,2-bis(3-bromo-4-hydroxy-5-isopropylphenyl)propane; 2,2-bis(3-t-butyl-5-chloro-4-hydroxyphenyl)propane; 2,2-bis(3-bromo-5-t-butyl-4-hydroxyphenyl)propane; 2,2-bis(3-chloro-5-phenyl-4-hydroxyphenyl)propane; 2,2-bis(3-bromo-5-phenyl-4-hydroxyphenyl)propane; 2,2-bis(3,5-dibromo-4-hydroxyphenyl)propane; 2,2-bis(3,5-di-t-butyl-4-hydroxyphenyl)propane; 2,2-bis(3,5-diisopropyl-4-hydroxyphenyl)propane; 2,2-bis(4-hydroxy-2,3,5,6-tetrachlorophenyl)propane; 2,2-bis(4-hydroxy-2,3,5,6-tetrabromophenyl)propane; 2,2-bis(4-hydroxy-2,3,5,6-tetramethylphenyl)propane; 2,2-bis(2,6-dichloro-3,5-dimethyl-4-hydroxyphenyl)propane; 2,2-bis(2,6-dibromo-3,5-dimethyl-4-hydroxyphenyl)propane; 1,1-bis(4-hydroxyphenyl)cyclohexane; 1,1-bis(3-chloro-4-hydroxyphenyl)cyclohexane; 1,1-bis(3-bromo-4-hydroxyphenyl)cyclohexane; 1,1-bis(4-hydroxy-3-methylphenyl)cyclohexane; 1,1-bis(4-hydroxy-3-isopropylphenyl)cyclohexane; 1,1-bis(3-t-butyl-4-hydroxyphenyl)cyclohexane; 1,1-bis(3-phenyl-4-hydroxyphenyl)cyclohexane; 1,1-bis(3,5-dichloro-4-hydroxyphenyl)cyclohexane; 1,1-bis(3,5-dibromo-4-hydroxyphenyl)cyclohexane; 1,1-bis(3,5-dimethyl-4-hydroxyphenyl)cyclohexane; 1,1-bis(3-chloro-4-hydroxy-5-methylphenyl)cyclohexane; 1,1-bis(3-bromo-4-hydroxy-5-methylphenyl)cyclohexane; 1,1-bis(3-chloro-4-hydroxy-5-isopropylphenyl)cyclohexane; 1,1-bis(3-bromo-4-hydroxy-5-isopropylphenyl)cyclohexane; 1,1-bis(3-t-butyl-5-chloro-4-hydroxyphenyl)cyclohexane; 1,1-bis(3-bromo-5-t-butyl-4-hydroxyphenyl)cyclohexane; 1,1-bis(3-chloro-5-phenyl-4-hydroxyphenyl)cyclohexane; 1,1-bis(3-bromo-5-phenyl- 4-hydroxyphenyl)cyclohexane; 1,1-bis(3,5-diisopropyl-4-hydroxyphenyl)cyclohexane; 1,1-bis(3,5-di-t-butyl-4-hydroxyphenyl)cyclohexane; 1,1-bis(3,5-diphenyl-4-hydroxyphenyl)cyclohexane; 1,1-bis(4-hydroxy-2,3,5,6-tetrachlorophenyl)cyclohexane; 1,1-bis(4-hydroxy-2,3,5,6-tetrabromophenyl)cyclohexane; 1,1-bis(4-hydroxy-2,3,5,6-tetramethylphenyl)cyclohexane; 1,1-bis(2,6-dichloro-3,5-dimethyl-4-hydroxyphenyl)cyclohexane; 1,1-bis(2,6-dibromo-3,5-dimethyl-4-hydroxyphenyl)cyclohexane; 1,1-bis(4-hydroxyphenyl)-3,3,5-trimethylcyclohexane; 1,1-bis(3-chloro-4-hydroxyphenyl)-3,3,5-trimethylcyclohexane; 1,1-bis(3-bromo-4-hydroxyphenyl)-3,3,5-trimethylcyclohexane; 1,1-bis(4-hydroxy-3-methylphenyl)-3,3,5-trimethylcyclohexane; 1,1-bis(4-hydroxy-3-isopropylphenyl)-3,3,5-trimethylcyclohexane; 1,1-bis(3-t-butyl-4-hydroxyphenyl)-3,3,5-trimethylcyclohexane; 1,1-bis(3-phenyl-4-hydroxyphenyl)-3,3,5-trimethylcyclohexane; 1,1-bis(3,5-dichloro-4-hydroxyphenyl)-3,3,5-trimethylcyclohexane; 1,1-bis(3,5-dibromo-4-hydroxyphenyl)-3,3,5-trimethylcyclohexane; 1,1-bis(3,5-dimethyl-4-hydroxyphenyl)-3,3,5-trimethylcyclohexane; 1,1-bis(3-chloro-4-hydroxy-5-methylphenyl)-3,3,5-trimethylcyclohexane; 1,1-bis(3-bromo-4-hydroxy-5-methylphenyl)-3,3,5-trimethyl-3,3,5-trimethylcyclohexane; 1,1-bis(3-chloro-4-hydroxy-5-isopropylphenyl)-3,3,5-trimethylcyclohexane; 1,1-bis(3-bromo-4-hydroxy-5-isopropylphenyl)-3,3,5-trimethylcyclohexane; 1,1-bis(3-t-butyl-5-chloro-4-hydroxyphenyl)-3,3,5-trimethylcyclohexane; 1,1-bis(3-bromo-5-t-butyl-4-hydroxyphenyl)-3,3,5-trimethylcyclohexane; 1,1-bis(3-chloro-5-phenyl-4-hydroxyphenyl)-3,3,5-trimethylcyclohexane; 1,1-bis(3-bromo-5-phenyl-4-hydroxyphenyl)-3,3,5-trimethylcyclohexane; 1,1-bis(3,5-diisopropyl-4-hydroxyphenyl)-3,3,5-trimethylcyclohexane; 1,1-bis(3,5-di-t-butyl-4-hydroxyphenyl)-3,3,5-trimethylcyclohexane; 1,1-bis(3,5-diphenyl-4-hydroxyphenyl)-3,3,5-trimethylcyclohexane; 1,1-bis(4-hydroxy-2,3,5,6-tetrachlorophenyl)-3,3,5-trimethylcyclohexane; 1,1-bis(4-hydroxy-2,3,5,6-tetrabromophenyl)-3,3,5-trimethylcyclohexane; 1,1-bis(4-hydroxy-2,3,5,6-tetramethylphenyl)-3,3,5-trimethylcyclohexane; 1,1-bis(2,6-dichloro-3,5-dimethyl-4-hydroxyphenyl)-3,3,5-trimethylcyclohexane; 1,1-bis(2,6-dibromo-3,5-dimethyl-4-hydroxyphenyl)-3,3,5-trimethylcyclohexane; 4,4'dihydroxy-3,5,3',5'-tetrabromo-1,1-biphenyl; 4,4'-dihydroxy-3,5,3',5'-tetramethyl-1,1-biphenyl; 4,4'-dihydroxy-3,3'-dimethyl-1,1-biphenyl; 4,4'-dihydroxy-3,5,3',5'-tetramethyldiphenylether; 4,4'-dihydroxy-3,5,3',5'-tetrabromodiphenylether; 4,4'-dihydroxy-3,5,3',5'-tetramethyldiphenylthioether; 1,3-bis(2-(3,5-dimethyl-4-hydroxyphenyl)-2-propyl)benzene and 1,3-bis(2-(3,5-dibromo-4-hydroxyphenyl)-2-propyl)benzene.

Suitable organic solvents which can be used are, for example, chlorinated aliphatic hydrocarbons, such as methylene chloride, chloroform, carbon tetrachloride, dichloroethane, trichloroethane, tetrachloroethane, dichloropropane and 1,2-dichloroethylene; substituted aromatic hydrocarbons such as, chlorobenzene, o-dichlorobenzene, and the various chlorotoluenes. The chlorinated aliphatic hydrocarbons, especially methylene chloride, are preferred.

Aqueous alkali or alkaline earth metal hydroxides can be used to adjust the pH of the reaction mixture prior to phosgenation, to maintain the pH of the reaction mixture during phosgenation and to maintain the pH of the reaction mixture following the addition of amine catalyst III. Some of the alkali metal or alkaline earth metal hydroxides, which can be employed are for example, sodium hydroxide, potassium hydroxide, and calcium hydroxide. Sodium and potassium hydroxides and particularly sodium hydroxide is preferred.

The identity of amine catalyst III employed in the method of the present invention plays a critical role in the successful conversion of hindered bisphenols into either high molecular weight polycarbonate or low molecular weight polycarbonate oligomers, as desired. The tertiary amine catalyst is likewise critical to the efficient preparation of diaryl carbonates of hindered phenols Tertiary aliphatic and cycloaliphatic amine catalysts III comprising at least one structural unit IIIa wherein the nitrogen has a valance of three are found to be superior to traditionally employed tertiary amine catalysts such as triethylamine. The data provided in Tables II and III show clearly that tertiary amines bearing one or two methyl groups outperform the traditionally employed triethylamine. Suitable amine catalysts III are illustrated by, but are not limited to, N,N-dimethylethylamine, N,N-dimethylpropylamine, N,N-dimethylbutylamine, N,N-dimethylpentylamine, N,N-dimethylhexylamine, N,N-dimethylheptylamine, N,N-dimethyloctylamine, N,N-dimethylnonylamine, N,N-dimethyldecylamine, N,N-dimethyldodecylamine, N,N-dimethylhexadecylamine, N,N-dimethyloctadecylamine, N,N-diethylmethylamine,

IIIa

N,N-dipropylmethylamine, N,N-dibutylmethylamine, N,N-dipentylmethylamine, N,N-dihexylmethylamine, N,N-didecylmethylamine, N-methylpyrrolidene, N-methylpiperidine, N-methylazacycloheptane, N-methylmorpholine, and 1,4-dimethylpipirazine.

One or more chain stoppers may be employed in the process of the instant invention and are used advantageously to limit the molecular weight of the product polycarbonate. Thus, in the absence of chain stopper or where it is present in relatively small amounts, for example less than 5 mole % based on the total amount of bisphenols employed, high molecular weight polycarbonates are formed. Where polycarbonate oligomers, rather than high molecular weight polymer, are desired the use of higher levels of chain stopper IV may be used. Using the method of the present invention polycarbonates comprising repeat units I having weight average molecular weights ($M_w$) ranging from about 500 to about 200,000 daltons may be prepared. Suitable chain stoppers are monofunctional phenols having structure IV

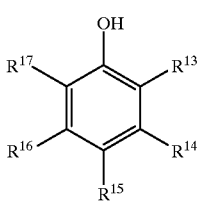

IV wherein $R^{13}$–$R^{17}$ are independently hydrogen, halogen, $C_1$-$C_{20}$ alkyl, $C_6$-$C_{20}$ aryl, $C_7$-$C_{21}$ aralkyl or $C_5$-$C_{20}$ cycloalkyl groups. Suitable chain stoppers IV are illustrated by but are not limited to phenol, p-cumylphenol, mesitol; 2,6-xylenol; 2,4-xylenol; 2,5-xylenol; 2,3,5-xylenol; 2,3,6-xylenol; 2,4,6-triethylphenol; 2,4-di-t-butylphenol; 3,5-di-t-butylphenol; 2,6-dimethyl-4-nonylphenol; 2,6-dibromophenol; 2,5-dibromo-phenol; 2,6-dichlorophenol; 2,5-dichlorophenol; 4-chloro-2,6-dibromophenol; 4-bromo-2,6-dichlorophenol; 2,4,6-tribromophenol; 2,3,6-tribromophenol; 2,4,6-trichlorophenol; 2,3,6-trichlorophenol; 2,6-dimethyl-4-bromophenol; 4-t-butyl-2,6-dimethylphenol; 2,6-di-t-butyl-4-methylphenol; 3-t-butyl-2,6-dimethyl phenol; 2,6-diphenylphenol; 2-phenylphenol; 2-methyl-6-phenylphenol; 2-methyl-4-phenyl-phenol; and 2,6-dimethyl-4-phenylphenol.

In some instances it may be advantageous to employ a phase transfer catalyst in the practice of the instant invention. Suitable phase transfer catalysts include tetraalkylammonium halides, tetraalkylammonium hydroxides, hexaalkylguanidium halides, N-alkylpyridinium halides, N-aralkylpyridinium halides, dialkylaminoquaternary ammonium halides, tetraalkylphosphonium halides, tetraalkylphosphonium hydroxides, alkyltriarylphosphonium halides and alkyltriarylphosphonium hydroxides. The phase transfer catalyst employed preferably comprises at least one cation selected from the group consisting of quaternary ammonium cations V

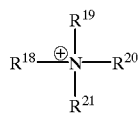

wherein $R^{18}$–$R^{21}$ are independently $C_1$-$C_{20}$ alkyl, $C_6$-$C_{20}$ aryl, $C_7$-$C_{21}$, aralkyl or $C_5$-$C_{20}$ cycloalkyl, and further $R^{18}$ and $R^{19}$ may together form a $C_4$-$C_{20}$ cycloaliphatic ring which may be substituted by one or more $C_1$-$C_{20}$ alkyl, $C_6$-$C_{20}$ aryl, $C_5$-$C_{21}$, aralkyl, $C_5$-$C_{20}$ cycloalkyl groups or a combination thereof;

guanidinium cations VI

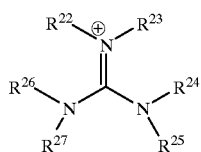

wherein $R^{22}$–$R^{27}$ are independently $C_1$-$C_{20}$ alkyl, $C_6$-$C_{20}$ aryl, $C_7$-$C_{21}$ aralkyl or $C_5$-$C_{20}$ cycloalkyl; pyridinium cations VII

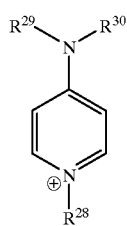

wherein $R^{28}$–$R^{30}$ are independently $C_1$-$C_{20}$ alkyl, $C_6$-$C_{20}$ aryl, $C_7$-$C_{21}$ aralkyl or $C_5$-$C_{20}$ cycloalkyl, and further $R^{29}$ and $R^{30}$ may together form a $C_4$-$C_{20}$ cycloaliphatic ring which may be substituted by one or more $C_1$-$C_{20}$ alkyl, $C_6$-$C_{20}$ aryl, $C_5$-$C_{21}$ aralkyl, $C_5$-$C_{20}$ cycloalkyl groups or a combination thereof; and diaminoalkylquaternary ammonium cations VIII

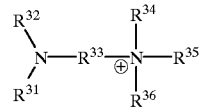

wherein each of $R^{31}$, $R^{32}$, $R^{34}$, $R^{35}$, and $R^{36}$ are $C_1$-$C_{20}$ aliphatic radicals, wherein said radicals $R^{31}$ and $R^{32}$ may together form a cycloaliphatic radical, said radicals $R^{34}$ and $R^{35}$ may together for a cycloaliphatic radical, $R^{33}$ is a $C_2$-$C_{20}$ aliphatic radical, a $C_5$-$C_{20}$ cycloaliphatic radical or a $C_4$-$C_{20}$ aromatic radical.

Suitable phase transfer catalysts are exemplified by tetrabutylphosphonium bromide, tetramethylphosphonium hydroxide, tetramethylammonium chloride, methyltributylammonium chloride, 1-benzyl-4-N,N-dimethylaminopyridinium chloride, hexaethylguanidinium chloride and 4-dimethylaminobutyltrimethylammonium chloride.

In one embodiment the present invention provides high molecular weight polycarbonates derived from sterically hindered bisphenols. The method of the present invention allows for molecular weight control of the product polycarbonate by inclusion of a chain stopper which limits the molecular weight of the product polymer. Where relatively low levels of chain stopper are employed or where the chain stopper is absent, very high molecular weight polycarbonates of sterically hindered bisphenols may be obtained. Polycarbonates comprising repeat units IX and

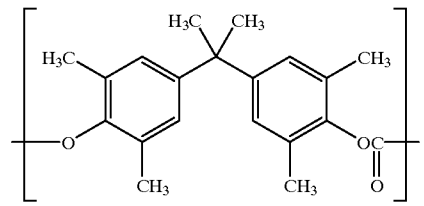

X may be obtained using the method of the present invention wherein said polycarbonates have a weight average molecular weight ($M_w$) ranging from 40,000 to 175,000 daltons.

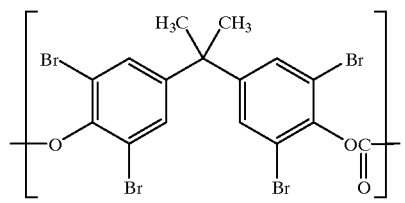

In other instances a large amount of chain stopper, more than 10 mole percent based upon the total moles of bisphenol II employed, may be used in order to provide low molecular weight oligomeric products.

In one embodiment of the present invention, steps (A) and (B) are carried out under conditions which convert bisphenol II into a low molecular weight oligomeric bischloroformate or alternatively a monomeric bischlorformate. The bis-chloroformate is then subsequently transformed into a polycarbonate. This can be effected by admixing bisphenol II with a solvent and water and introducing between about 2.01 and about 2.75 equivalents of phosgene into the mixture at a pH in the range between about 5 and about 8.5. When all of the bisphenol hydroxyl groups have been consumed, the reaction mixture is sparged with nitrogen to remove any unreacted phosgene. The crude product is then subjected to steps (C) and (D) to afford high molecular weight polycarbonate incorporating repeat units I.

Whether the polycarbonate product has high or low molecular weight, its principal use is in the preparation of molded articles having improved physical properties such as greater fire resistance, higher glass transition temperature, greater resistance to water absorption or increased hydrolytic stability. The polycarbonates produced by the method of the present invention may be blended with other polymers such as bisphenol A polycarbonate prior to transformation into a molded article.

The desired molded article may be obtained by molding the polycarbonate prepared by the method of the present invention or alternatively molding a blend of said polycarbonate with another polycarbonate, a copolycarbonate, a copolyestercarbonate or a polyester by injection molding, compression molding, extrusion methods and solution casting methods. Injection molding is the more preferred method of forming the article.

In a further embodiment, the present invention provides a method for the preparation of symmetrical diaryl carbonates having structure XI

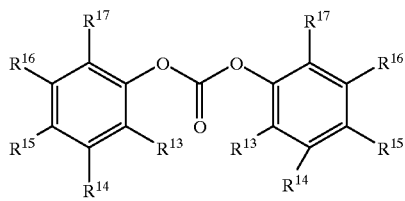

XI said method comprising:
(A') admixing at least one solvent, water, and optionally one or more phase transfer catalysts, with at least one phenol having structure IV

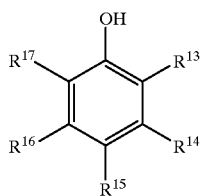

IV (B') adding phosgene and sufficient aqueous base to maintain a pH in a range between about 5 and about 8.5; said phosgene being added incrementally in an amount equivalent to between about 1.01 to about 1.5 equivalents based upon the amount of phenol used in step (A');
(C') adding from about 3 to about 4 molar equivalents relative to the amount of phenol used in step (A') of aqueous base and a catalyst in an amount corresponding to between about 0.001 and about 0.10 molar equivalents based upon the amount of phenol used in step (A'), said catalyst having structure III; and
(D') agitating the mixture formed by steps (A'), (B') and (C') at a pH in a range between about 8 and about 13 until said mixture is free of chloroformate groups.

In one embodiment the present invention provides a method to prepare diaryl carbonates from hindered phenols in which steps (A') and (C') precede step (B').

Suitable hindered phenols for use in the preparation of hindered diaryl carbonates are monofunctional phenols IV wherein $R^{13}-R^{17}$ are independently hydrogen, halogen, $C_1-C_{20}$ alkyl, $C_6-C_{20}$ aryl, $C_7-C_{21}$ aralkyl or $C_5-C_{20}$ cycloalkyl groups. Suitable hindered phenols IV are illustrated by, but are not limited to mesitol, 2,6-xylenol; 2,4-xylenol; 2,5-xylenol; 2,3,5-xylenol; 2,3,6-xylenol; 2,4,6-triethylphenol; 2,4-di-t-butylphenol; 3,5-di-t-butylphenol; 2,6-dimethyl-4-nonylphenol; 2,6-dibromophenol; 2,5-dibromophenol; 2,6-dichlorophenol; 2,5-dichlorophenol; 4-chloro-2,6-dibromophenol; 4-bromo-2,6-dichlorophenol; 2,4,6-tribromophenol; 2,3,6-tribromophenol; 2,4,6-trichlorophenol; 2,3,6-trichlorophenol; 2,6-dimethyl-4-bromophenol; 4-t-butyl-2,6-dimethylphenol; 2,6-di-t-butyl-4-methylphenol; 3-t-butyl-2,6-dimethyl phenol; 2,6-diphenylphenol; 2-phenylphenol; 2-methyl-6-phenylphenol; 2-methyl-4-phenylphenol; and 2,6-dimethyl-4-phenylphenol.

Suitable organic solvents which can be used in the method to prepare hindered diaryl carbonates are, for example, chlorinated aliphatic hydrocarbons, such as methylene chloride, chloroform, carbon tetrachloride, dichloroethane, trichloroethane, tetrachloroethane, dichloropropane and 1,2-dichloroethylene; substituted aromatic hydrocarbons such as, chlorobenzene, o-dichlorobenzene, and the various chlorotoluenes. The chlorinated aliphatic hydrocarbons, especially methylene chloride, are preferred.

Aqueous alkali, or alkaline earth metal hydroxides can be used to adjust the pH of the mixture of hindered phenol, solvent and water prior to phosgenation, to maintain the pH of the reaction mixture during phosgenation and to maintain the pH of the reaction mixture following the addition of amine catalyst III. Some of the alkali metal or alkaline earth metal hydroxides which can be employed are for example, sodium hydroxide, potassium hydroxide, and calcium hydroxide. Sodium and potassium hydroxides and particularly sodium hydroxide is preferred.

Suitable phase transfer catalysts which can be used in the method to prepare hindered diaryl carbonates include tetraalkylammonium halides, hexaalkylguanidium halides, N-alkylpyridinium halides, N-aralkylpyridinium halides dialkylaminoquaternary ammonium halides, tetraalkylphosphonium halides, tetraalkylphosphonium hydroxides, alkyltriarylphosphonium halides and alkyltriarylphosphonium hydroxides. Suitable phase transfer catalysts are exemplified by tetrabutylphosphonium bromide, tetramethylphosphonium hydroxide, tetramethylammonium chloride, methyltributylammonium chloride, 4-N,N-dimethylamino-N-benzylpyridinium chloride, hexaethylguanidinium chloride and 4-dimethylaminobutyltrimethylammonium chloride.

The following examples are set forth to provide those of ordinary skill in the art with a detailed description of how the methods claimed herein are made and evaluated, and are not intended to limit the scope of what the inventors regard as their invention. Unless indicated otherwise, parts are by weight, temperature is in °C.

Molecular weights are reported as weight average ($M_w$) molecular weight and were determined by GPC analysis, using polystyrene standards to construct a calibration curve against which polymer molecular weights were determined. The temperature of the columns was about 25° C. and the mobile phase was chloroform. Testing for the presence of chloroformates was carried out with commercially available phosgene detection paper, such as Chemcasette SP from MDA Scientific of Lincolnshire, Ill., by spotting a portion of the reaction mixture onto the test paper. Oligomeric products were analyzed by HPLC.

EXAMPLE 1

A 1 liter 5-neck Morton flask equipped with a mechanical stirrer, pH electrode, caustic addition port, phosgene dip tube and chilled brine condenser vented to a phosgene scrubber was charged with 2,2-bis(3,5-dimethyl-4-hydroxyphenyl)propane (TMBPA, 56.8 g, 200 mmol), mesitol (816 mg, 6 mmol), methylene chloride (300 mL), water (100 mL), and 1 gram of a 75% methyltributyl ammonium chloride (MTBA) solution in water. The mixture was stirred and phosgene was introduced via a mass flow meter at a rate of 1.25 g per minute for a period of 18.5 minutes (23.1 g $COCl_2$, 1.15 equivalents). During the phosgene addition 50% aqueous sodium hydroxide solution was added dropwise in an amount sufficient to maintain a pH between about 13.5 and about 14. Aqueous caustic addition was effected with a peristaltic pump equipped with a pH sensitive feedback controller. Upon completion of phosgene addition the reaction mixture tested positive for the presence of chloroformate groups. N,N-dimethylbutylamine (DMBA, 0.18 mL, 1.28 mmole) was added and the reaction mixture was stirred at ambient temperature for about 10 minutes at which point no chloroformates were detected. The resulting polycarbonate had a weight average molecular weight ($M_w$) of 49,600 daltons.

EXAMPLE 2

A reaction vessel equipped as in Example 1 was charged with methylene chloride, water, 2,2-bis(3,5-dimethyl-4-hydroxyphenyl)propane, and N-methyltributylammonium chloride solution in the amounts indicated in Example 1. Phosgene (20.1 g) was introduced at 1.25 g/min at a pH between about 13.5 and about 14. Following phosgene addition the mixture tested positive for the presence of chloroformate groups. Additional phosgene (0.1 equivalents) was added over a five minute period. Next, N,N-dimethylbutylamine (0.05 mL, 0.4 mmole) was added and the reaction mixture was stirred at ambient temperature for about 10 minutes at which point no chloroformates were detected. The resulting polycarbonate had a weight average molecular weight (Mw) of 53,500 daltons.

Examples 3–5 were carried as in Example 2.

TABLE I

| Example | bisphenol[a] | mesitol | phosgene[b] | DMBA[c] | Mw[d] |
|---|---|---|---|---|---|
| 1 | 200 mmol | 6 mmol | 15% | 1.28 mmol | 49600 |
| 2 | 200 mmol | 6 mmol | 10% | 0.4 mmol | 53,500 |
| 3 | 200 mmol | 6 mmol | 5% | 0.7 mmol | 45,000 |
| 4 | 200 mmol | 3 mmol | 10% | 0.4 mmol | 94,300 |
| 5 | 200 mmol | 6 mmol | 10% | 0.4 mmol | 53,300 |

[a]2,2-bis(3,5-dimethyl-4-hyrdoxyphenyl)propane.
[b]mole % excess phosgene relative to bisphenol and mesitol employed as chain stopper.
[c]N,N-dimthylbutylamine
[d]Weight average molecular weight Examples 1–5 illustrate the use of the method of the present invention to prepare high molecular weight polycarbonate from a hindered bisphenol, 2,2-bis(3,5-dimethyl-4-hydroxyphenyl)propane, in which only modest amounts (5–15 mole percent) of excess phosgene are required.

EXAMPLE 6

To a flask equipped as in example 1 was charged 2,2-bis (3,5-dibromo-4-hydroxyphenyl)propane (TBBPA, 69.56 g, 127.9 mmol), methylene chloride (70 mL), water (65 mL), mesitol (6.1 mL of a 5% solution in methylene chloride), 1-dimethylaminododecane (11 mL of a 5% solution in methylene chloride). The pH was adjusted to about 13 by the addition of 50% aqueous sodium hydroxide solution and the mixture was stirred for 3 minutes. Phosgene was then introduced at a rate of 0.80 g/min for a period of 20 minutes while the mixture was stirred vigorously. During the phosgene addition 50% aqueous sodium hydroxide solution was added dropwise in an amount sufficient to maintain a pH of about 13. Following phosgene addition the organic layer was separated from the brine layer and washed successively with 3% hydrochloric acid and water. An analytical sample was then removed for molecular weight measurement and cast film preparation.

Examples 7–9 and Comparative Example 1 were carried out using the method of Example 6 while varying the amounts of catalyst and chain stopper used. In Example 9 bisphenol A (BPA) was used instead of TBBPA. In Comparative Example 1 the catalyst of Examples 6–9 was replaced with triethylamine.

TABLE II

| Example | Monomer | Catalyst | Mole % Catalyst | Chain-stopper | Mole % Chain-stopper | $M_w$[e] |
|---|---|---|---|---|---|---|
| 6 | TBBPA[a] | DMAD[b] | 2.0 | mesitol | 3.5 | 46,200 |
| 7 | TBBPA | DMAD | 2.0 | none | 0 | 157,400 |
| 8 | TBBPA | DMAD | 2.0 | TBP[c] | 3.0 | 113,400 |
| 9 | BPA | DMAD | 0.5 | xylenol[d] | 3.5 | 43,500 |
| CE-1[f] | TBBPA | Et$_3$N | 4.0 | none | 0 | 20,600 |

[a]2,2-bis(3,5-dibromo-4-hyrdoxyphenyl)propane.
[b]N,N-dimethylaminododecane
[c]2,4,6-tribromophenol
[d]2,6-xylenol
[e]Weight average molecular weight
[f]Comparative Example No. 1.

Examples 6–8 illustrate the use of the method of the present invention to prepare high molecular weight polycarbonate from 2,2-bis(3,5-dibromo-4-hyrdoxyphenyl) propane. Example 9 shows that the method of the present invention is applicable to the preparation of bisphenol A polycarbonate. Comparative Example 1 illustrates the relative ineffectiveness of triethylamine as a catalyst for making hindered polycarbonates such as that prepared from 2,2-bis (3,5-dibromo-4-hyrdoxyphenyl)propane (TBBPA).

EXAMPLE 10

To a flask equipped as in example 1 was charged the bischloroformate of 2,2-bis(3,5-dibromo-4-hydroxyphenyl) propane (BCF), methylene chloride, water, and N,N-dimethylaminododecane (DMAD, 0.5 mole % based on the amount of BCF). The mixture was stirred vigorously for 30 seconds during which time 50% aqueous sodium hydroxide solution was added dropwise in an amount sufficient to maintain a pH of about 11. The organic layer was then separated from the brine layer and washed successively with 3% hydrochloric acid and water. An analytical sample was then removed for molecular weight measurement and cast film preparation.

Comparative Example 2 was carried out as in Example 10 except that triethylamine was used as the catalyst and the reaction time was lengthened to 4 minutes.

TABLE III

| Example | Monomer | Catalyst | Mole % Catalyst | Chain-stopper | Mole % Chain-stopper | $M_w{}^d$ |
|---|---|---|---|---|---|---|
| 10 | BCF[b] | DMAD[c] | 0.5 | none | 0 | 161,000 |
| CE-2[a] | BCF[b] | Et$_3$N | 0.5 | none | 0 | 156,000 |

[a]Comparative Example No. 2.
[b]bischloroformate of TBBPA
[c]N,N-dimethylaminododecane
[d]Weight average molecular weight

EXAMPLE 11

A reaction vessel equipped as in Example 1 was charged with TBBPA (27.2 g, 0.050 mol), 2,4,6-tribromophenol (4.41 g, 0.0133 mol), methylene chloride (150 ml), water (50 ml), and methyltributyl ammonium chloride phase transfer catalyst (0.205 ml of 75% solution, 0.625 mmol, 1 mol %). Phosgene (6.25g, 1.10 eq.) was added to the reaction at 0.5 g/min with reaction pH being controlled at 9.5–10.0 by addition of 25% NaOH solution. When the phosgene addition was complete the pH was adjusted to 11 and N,N-dimethylethylamine (0.0625 mmol, 13.6 microliters, 0.1 mol %) was added to the reaction. The pH of the reaction mixture dropped rapidly and sufficient additional 25% NaOH solution was added to stabilize the pH above 11. At this point a high level of chloroformates remained in solution as evidenced by a strong response of phosgene detection paper to a drop of reaction mixture. Additional N,N-dimethylethylamine (0.25 mmol) was added in four equal portions and the reaction mixture was stirred at pH 11 until chloroformates were no longer detectable. The brine layer was shown by uv-visible spectroscopy to be free of phenolics thereby attesting to the complete incorporation of monomer and chainstopper into the product. The organic phase of the reaction was stored over 1N HCl for subsequent analysis. HPLC analysis showed a well defined mixture of polycarbonate oligomers of TBBPA having an average degree of oligomerization of about 5. HPLC analysis further revealed less than 1% tribromophenyl carbonate and no urethanes.

Comparative Example 3 (TEA Control)

The reaction was formulated as in example 11 except triethylamine (6.25 mmol, 0.870 ml, 10 mol %) was added instead of the phase transfer catalyst. Phosgene (8.5 g, 1.50 eq.) was added at 0.5 g/min and the pH was controlled at 11 by caustic addition. Chloroformates were detected in the in the reaction mixture for a period of 10 minutes following phosgene addition. The brine and organic phases were separated and the organic phase was stored over 1N HCl. HPLC analysis of the organic phase showed 7.5% tribromophenyl carbonate and detectable levels of urethanes together with a distribution of polycarbonate oligomers of TBBPA having an average degree of oligomerization of about 5.

EXAMPLE 12

The reaction was formulated as in Example 11 except the order of addition of tribromophenol was changed. Phosgenation was carried out as in Example 11 and just prior to the addition of the dimethylethylamine the tribromophenol was added. As in Example 11, additional amine catalyst was required in order to consume the chloroformates. Analysis of the product mixture as in Example 11 showed 6.6% tribromophenyl carbonate and a trace of urethanes and a TBBPA polycarbonate having a degree of oligomerization of about 5.

EXAMPLE 13

Reaction was formulated as in example 11 and phosgene (5.70 g, 1.02 eq.) was delivered at 0.5 g/min at pH 10. When phosgene addition was complete the pH was adjusted to 11 and N,N-dimethylethylamine (0.0625 mmol, 13.6 ul, 0.1 mol %) was added. The pH of the mixture was maintained at 11 by the addition of 25% NaOH solution. After the last of the caustic was added the mixture was stirred briefly (1–2 minutes) until chloroformates could no longer be detected. HPLC analysis of the organic layer showed no tribromophenyl carbonate or urethanes to be present and a TBBPA polycarbonate having a degree of oligomerization of about 5.

TABLE IV

| Example | Catalyst[a] | Mole % Cat. | Mole % CS[b] | excess COCl$_2$[c] | PTC[d] | Mole % PTC | Yield TBPC[e] | UBPD?[f] |
|---|---|---|---|---|---|---|---|---|
| 11 | DMEA[c] | 0.1 | 25 | 10 | MTBA | 1 | 1%> | no |
| CE-3[g] | Et$_3$N | 10 | 25 | 50 | — | 0 | 7.5% | yes |
| 12 | DMEA | 0.5 | 25 | 10 | MTBA | 1 | 6.6% | yes |
| 13 | DMEA | 0.1 | 25 | 2 | MTBA | 1 | 1%> | no |

[a]Amine catalyst, DMEA = N.N-dimethylethylamine
[b]CS = chainstopped, TBP = 2,4,6-tribromophenol
[c]Mole % excess phosgene
[d]PTC = Phase transfer catalyst, MTBA = methyltributylammonium chloride
[e]Yield of bis(2,4,6-tribromophenyl) carbonate.
[f]Urethane by-product detected?
[g]Comparative Example No. 3

Examples 11–13 illustrate the use of the method of the present invention in the preparation of polycarbonate oligomers using only a slight excess of phosgene. Example 13, for example, uses only about 2 percent excess phosgene. Comparative Example 3 (CE-3), in which a large excess of phosgene was required, illustrates the ineffectiveness of triethylamine as a catalyst in this transformation relative to the catalysts of the present invention. In addition, the use of triethylamine results in significant amounts of urethane and coupled chainstopper, bis(2,4,6-tribromophenyl) carbonate, formation. Example 12 illustrates the preference for lower levels of catalyst and early addition of chainstopper when preparing polycarbonate oligomers by the method of the present invention.

EXAMPLE 14

The reaction apparatus described in example 11 was charged with 2,4,6-tribromophenol (33.0 g, 0.1 mol), methylene chloride (200 ml), and water (30 ml). Phosgene (10.1 g, 0.102 mol, 1.02 eq.) was added to the reaction while the pH was maintained at 8 by the addition of 25% NaOH. Upon completion of phosgene addition it was noted that approximately 0.15 mol of caustic had been consumed indicating that some degree of hydrolysis of either phosgene or chloroformates had occurred. To increase the potential yield of the desired product, additional phosgene (4.95 g, 0.05 mol) was added at pH 5. The pH of the reaction was then adjusted to 9 to consume any condensed phosgene. The brine was discarded and the organic layer retained for isolation and purification of the desired product. A portion of the organic layer (70 mL) was combined with 125 mmol of NaOH diluted to 0.2 M. Fifty microliters of dimethylbutylamine was added and the mixture was stirred for 30 minutes. The reaction mixture was then treated with 3 M HCl, 0.1 M HCl, then water. Evaporation of the methylene chloride afforded a white solid which was identified as the tribromophenyl carbonate by HPLC.

Example 14 illustrates an embodiment of the present invention in which, in the absence of a bisphenol, hindered monophenols are efficiently converted to diaryl carbonates.

The invention has been described in detail with particular reference to preferred embodiments thereof, but it will be understood by those skilled in the art that variations and modifications can be effected within the spirit and scope of the invention.

What is claimed is:

1. A method for making a polycarbonate comprising structural units I

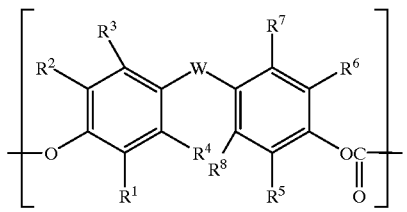

I wherein $R^1$–$R^8$ are independently hydrogen, halogen, $C_1$-$C_{20}$ alkyl, $C_6$-$C_{20}$ aryl, $C_7$-$C_{21}$ aralkyl or $C_5$-$C_{20}$ cycloalkyl;

W is a bond, an oxygen atom, a sulfur atom, a $SO_2$ group, a $C_6$–$C_{20}$ aromatic radical, a $C_6$–$C_{20}$ cycloaliphatic radical or the group

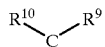

wherein $R^9$ and $R^{10}$ are independently hydrogen, $C_1$-$C_{20}$ alkyl, $C_6$-$C_{20}$ aryl, $C_7$-$C_{21}$, aralkyl or $C_5$-$C_{20}$ cycloalkyl, or $R^9$ and $R^{10}$ together form a $C_4$-$C_{20}$ cycloaliphatic ring which is optionally substituted by one or more $C_1$-$C_{20}$ alkyl, $C_6$-$C_{20}$ aryl, $C_5$-$C_{21}$ aralkyl, $C_5$-$C_{20}$ cycloalkyl groups or a combination thereof;

said method comprising:

(A) admixing a solvent, water, optionally one or more phase transfer catalysts and optionally one or more chain stoppers, with at least one bisphenol having structure II

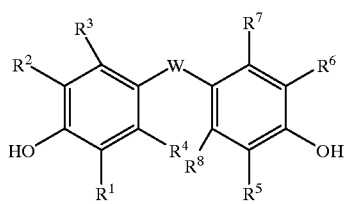

II (B) adding phosgene and sufficient aqueous base to maintain a pH in a range between about 11 and about 14; said phosgene being added incrementally in an amount equivalent to between about 1.01 and about 1.75 equivalents based upon the amount of bisphenol used in step (A);

(C) adding a catalyst in an amount corresponding to between about 0.001 and about 0.10 equivalents based upon the amount of bisphenol used in step (A), said catalyst being selected from the group consisting of N,N-dimethylethylamine, N,N-dimethylpropylamine, N,N-dimethylbutylamine, N,N-dimethylpentylamine, N,N-dimethylhexylamine, N,N-dimethylheptylamine, N,N-dimethyloctylamine, N,N-dimethylnonylamine, N,N-dimethyldecylamine, N,N-dimethyldodecylamine, N,N-dimethylhexadecylamine, N,N-dimethyloctadecylamine; and (D) agitating the mixture formed by steps (A), (B) and (C) at a pH in a range between about 8 and about 14 until said mixture is free of chloroformate groups.

2. A method according to claim 1 wherein said solvent is selected from among the group consisting of chlorinated aliphatic hydrocarbons and substituted aromatic hydrocarbons.

3. A method according to claim 1 wherein said phase transfer catalyst is selected from among the group consisting of quaternary ammonium salts, guanidinum salts, pyridinium salts, and phosphonium salts.

4. A method according to claim 3 wherein the amount of said phase transfer catalyst employed is in a range between 0 and about 5 mole percent based on the total number of moles of bisphenol employed.

5. A method according to claim 1 wherein said chain stopper is at least one monofunctional phenol having structure IV

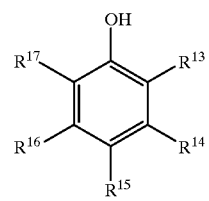

IV wherein $R^{13}$–$R^{17}$ are independently hydrogen, halogen, $C_1$-$C_{20}$ alkyl, $C_6$-$C_{20}$ aryl, $C_7$-$C_{21}$ aralkyl or $C_5$-$C_{20}$ cycloalkyl groups.

6. A method according to claim 5 wherein the amount of said chain stopper employed is in a range between 0 and about 40 mole percent based on the total number of moles of bisphenol employed.

7. A method according to claim 5 wherein said chain stopper is selected from the group consisting of phenol, p-cumylphenol, mesitol, 2,6-xylenol; 2,4-xylenol; 2,5-xylenol; 2,3,5-xylenol; 2,3,6-xylenol; 2,4,6-triethylphenol; 2,4-di-t-butylphenol; 3,5-di-t-butylphenol; 2,6-dimethyl-4-nonylphenol; 2,6-dibromophenol; 2,5-dibromophenol; 2,6-dichlorophenol; 2,5-dichlorophenol; 4-chloro-2,6-dibromophenol; 4-bromo-2,6-dichlorophenol; 2,4,6-tribromophenol; 2,3,6-tribromophenol; 2,4,6-trichlorophenol; 2,3,6-trichlorophenol; 2,6-dimethyl-4-bromophenol; 4-t-butyl-2,6-dimethylphenol; 2,6-di-t-butyl-4-methylphenol; 3-t-butyl-2,6-dimethyl phenol; 2,6-diphenylphenol; 2-phenylphenol; 2-methyl-6-phenylphenol; 2-methyl-4-phenyl-phenol; and 2,6-dimethyl-4-phenylphenol.

8. A method according to claim 1 wherein said phase transfer catalyst comprises cations selected from the group consisting of quaternary ammonium cations V

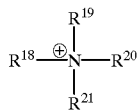

wherein $R^{18}$–$R^{21}$ are independently $C_1$-$C_{20}$ alkyl, $C_6$-$C_{20}$ aryl, $C_7$-$C_{21}$ aralkyl or $C_5$-$C_{20}$ cycloalkyl, and further $R^{18}$ and $R^{19}$ may together form a $C_4$-$C_{20}$ cycloaliphatic ring which may be substituted by one or more $C_1$-$C_{20}$ alkyl, $C_6$-$C_{20}$ aryl, $C_5$-$C_{21}$ aralkyl, $C_5$-$C_{20}$ cycloalkyl groups or a combination thereof;

guanidinium cations VI

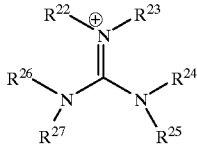

wherein $R^{22}$–$R^{27}$ are independently $C_1$-$C_{20}$ alkyl, $C_6$-$C_{20}$ aryl, $C_7$-$C_{21}$ aralkyl or $C_5$-$C_{20}$ cycloalkyl;

pyridinium cations VII

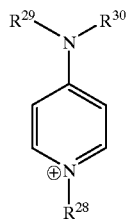

wherein $R^{28}$–$R^{30}$ are independently $C_1$-$C_{20}$ alkyl, $C_6$-$C_{20}$ aryl, $C_7$-$C_{21}$ aralkyl or $C_5$-$C_{20}$ cycloalkyl, and further $R^{29}$ and $R^{30}$ may together form a $C_4$-$C_{20}$ cycloaliphatic ring which may be substituted by one or more $C_1$-$C_{20}$ alkyl, $C_6$-$C_{20}$ aryl, $C_5$-$C_{21}$ aralkyl, $C_5$-$C_{20}$ cycloalkyl groups or a combination thereof; and diaminoalkyl quaternary ammonium salts VIII

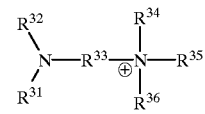

wherein each $R^{31}$, $R^{32}$, $R^{34}$, $R^{35}$, and $R^{36}$ are $C_1$–$C_{20}$ aliphatic radicals, wherein said radicals $R^{31}$ and $R^{32}$ may together form a cycloaliphatic radical, said radicals $R^{34}$ and $R^{35}$ may together for a cycloaliphatic radical, $R^{33}$ is a $C_2$–$C_{20}$ aliphatic radical, a $C_5$–$C_{20}$ cycloaliphatic radical or a $C_4$–$C_{20}$ aromatic radical.

9. A method according to claim 1 wherein said bisphenols are selected from the group consisting of 2,2-bis(4-hydroxyphenyl)propane (bisphenol A); 2,2-bis(3-chloro-4-hydroxyphenyl)propane; 2,2-bis(3-bromo-4-hydroxyphenyl)propane; 2,2-bis(4-hydroxy-3-methylphenyl)propane; 2,2-bis(4-hydroxy-3-isopropylphenyl)propane; 2,2-bis(3-t-butyl-4-hydroxyphenyl)propane; 2,2-bis(3-phenyl-4-hydroxyphenyl)propane; 2,2-bis(3,5-dichloro-4-hydroxyphenyl)propane; 2,2-bis(3,5-dibromo-4-hydroxyphenyl)propane; 2,2-bis(3,5-dimethyl-4-hydroxyphenyl)propane; 2,2-bis(3-chloro-4-hydroxy-5-methylphenyl)propane; 2,2-bis(3-bromo-4-hydroxy-5-methylphenyl)propane; 2,2-bis(3-chloro-4-hydroxy-5-isopropylphenyl)propane; 2,2-bis(3-bromo-4-hydroxy-5-isopropylphenyl)propane; 2,2-bis(3-t-butyl-5-chloro-4-hydroxyphenyl)propane; 2,2-bis(3-bromo-5-t-butyl-4-hydroxyphenyl)propane; 2,2-bis(3-chloro-5-phenyl-4-hydroxyphenyl)propane; 2,2-bis(3-bromo-5-phenyl-4-hydroxyphenyl)propane; 2,2-bis(3,5-diisopropyl-4-hydroxyphenyl)propane; 2,2-bis(3,5-di-t-butyl-4-hydroxyphenyl)propane; 2,2-bis(3,5-diphenyl-4-hydroxyphenyl)propane; 2,2-bis(4-hydroxy-2,3,5,6-tetrachlorophenyl)propane; 2,2-bis(4-hydroxy-2,3,5,6-tetrabromophenyl)propane; 2,2-bis(4-hydroxy-2,3,5,6-tetramethylphenyl)propane; 2,2-bis(2,6-dichloro-3,5-dimethyl-4-hydroxyphenyl)propane; 2,2-bis(2,6-dibromo-3,5-dimethyl-4-hydroxyphenyl)propane; 1,1-bis(4-hydroxyphenyl)cyclohexane; 1,1-bis(3-chloro-4-hydroxyphenyl)cyclohexane; 1,1-bis(3-bromo-4-hydroxyphenyl)cyclohexane; 1,1-bis(4-hydroxy-3-methylphenyl)cyclohexane; 1,1-bis(4-hydroxy-3-isopropylphenyl)cyclohexane; 1,1-bis(3-t-butyl-4-hydroxyphenyl)cyclohexane; 1,1-bis(3-phenyl-4-hydroxyphenyl)cyclohexane; 1,1-bis(3,5-dichloro-4-hydroxyphenyl)cyclohexane; 1,1-bis(3,5-dibromo-4-hydroxyphenyl)cyclohexane; 1,1-bis(3,5-dimethyl-4-hydroxyphenyl)cyclohexane; 1,1-bis(3-chloro-4-hydroxy-5-methylphenyl)cyclohexane; 1,1-bis(3-bromo-4-hydroxy-5-methylphenyl)cyclohexane; 1,1-bis(3-chloro-4-hydroxy-5-isopropylphenyl)cyclohexane; 1,1-bis(3-bromo-4-hydroxy-5-isopropylphenyl)cyclohexane; 1,1-bis(3-t-butyl-5-chloro-4-hydroxyphenyl)cyclohexane; 1,1-bis(3-bromo-5-t-butyl-4-hydroxyphenyl)cyclohexane; bis(3-chloro-5-phenyl-4-hydroxyphenyl)cyclohexane; 1,1-bis(3-bromo-5-phenyl-4-hydroxyphenyl)cyclohexane; 1,1-bis(3,5-diisopropyl-4-hydroxyphenyl)cyclohexane; 1,1-bis(3,5-di-t-butyl-4-hydroxyphenyl)cyclohexane; 1,1-bis(3,5-diphenyl-4-hydroxyphenyl)cyclohexane; 1,1-bis(4-hydroxy-2,3,5,6-tetrachlorophenyl)cyclohexane; 1,1-bis(4-hydroxy-2,3,5,6-tetrabromophenyl)cyclohexane; 1,1-bis(4-hydroxy-2,3,5,6-tetramethylphenyl)cyclohexane; 1,1-bis(2,6-dichloro-3,5-dimethyl-4-hydroxyphenyl)cyclohexane; 1,1-bis(2,6- dibromo-3,5-dimethyl-4-hydroxyphenyl)cyclohexane; 1,1-bis(4-hydroxyphenyl)-3,3,5-trimethylcyclohexane; 1,1-bis(3-chloro-4-hydroxyphenyl)-3,3,5-trimethylcyclohexane; 1,1-bis(3-bromo-4-hydroxyphenyl)-3,3,5-trimethylcyclohexane; 1,1-bis(4-hydroxy-3-methylphenyl)-3,3,5-trimethylcyclohexane; 1,1-bis(4-hydroxy-3-isopropylphenyl)-3,3,5-trimethylcyclohexane; 1,1-bis(3-t-butyl-4-hydroxyphenyl)-3,3,5-trimethylcyclohexane; 1,1-bis(3-phenyl-4-hydroxyphenyl)-3,3,5-trimethylcyclohexane; 1,1-bis(3,5-dichloro-4-hydroxyphenyl)-3,3,5-trimethylcyclohexane; 1,1-bis(3,5-dibromo-4-hydroxyphenyl)-3,3,5-trimethylcyclohexane; 1,1-bis(3,5-dimethyl-4-hydroxyphenyl)-3,3,5-trimethylcyclohexane; 1,1-bis(3-chloro-4-hydroxy-5-methylphenyl)-3,3,5-trimethylcyclohexane; 1,1-bis(3-bromo-4-hydroxy-5-methylphenyl)-3,3,5-trimethyl-3,3,5-trimethylcyclohexane; 1,1-bis(3-chloro-4-hydroxy-5-isopropylphenyl)-3,3,5-trimethylcyclohexane; 1,1-bis(3-bromo-4-hydroxy-5-isopropylphenyl)-3,3,5-trimethylcyclohexane; 1,1-bis(3-t-butyl-5-chloro-4-hydroxyphenyl)-3,3,5-trimethylcyclohexane; 1,1-bis(3-bromo-5-t-butyl-4-hydroxyphenyl)-3,3,5-trimethylcyclohexane; 1,1-bis(3-chloro-5-phenyl-4-hydroxyphenyl)-3,3,5-trimethylcyclohexane; 1,1-bis(3-bromo-5-phenyl-4-hydroxyphenyl)-3,3,5-trimethylcyclohexane; 1,1-bis(3,5-diisopropyl-4-hydroxyphenyl)-3,3,5-trimethylcyclohexane; 1,1-bis(3,5-di-t-butyl-4-hydroxyphenyl)-3,3,5-trimethylcyclohexane; 1,1-bis(3,5-diphenyl-4-hydroxyphenyl)-3,3,5-trimethylcyclohexane; 1,1-bis(4-hydroxy-2,3,5,6-tetrachlorophenyl)-3,3,5-trimethylcyclohexane; 1,1-bis(4-hydroxy-2,3,5,6-tetrabromophenyl)-3,3,5-trimethylcyclohexane; 1,1-bis(4-hydroxy-2,3,5,6-tetramethylphenyl)-3,3,5-trimethylcyclohexane; 1,1-bis(2,6-dichloro-3,5-dimethyl-4-hydroxyphenyl)-3,3,5-trimethylcyclohexane; 1,1-bis(2,6-dibromo-3,5-dimethyl-4-hydroxyphenyl)-3,3,5-trimethylcyclohexane; 4,4'dihydroxy-3,5,3',5'-tetrabromo-1,1-biphenyl; 4,4'-dihydroxy-3,5,3',5'-tetramethyl-1,1-biphenyl; 4,4'-dihydroxy-3,3'-dimethyl-1,1-biphenyl; 4,4'-dihydroxy-3,5,3',5'-tetramethyldiphenylether; 4,4'-dihydroxy-3,5,3',5'-tetrabromodiphenylether; 4,4'-dihydroxy-3,5,3',5'-tetramethyldiphenylthioether; 1,3-bis(2-(3,5-dimethyl-4-hydroxyphenyl)-2-propyl)benzene and 1,3-bis(2-(3,5-dibromo-4-hydroxyphenyl)-2-propyl)benzene.

10. A method according to claim 1 wherein said solvent is methylene chloride.

11. A method according to claim 1 wherein the polycarbonate comprising structural units I has a weight average molecular weight of between about 500 and about 200,000 daltons.

12. A method according to claim 1 in which the order of steps is (A) then (B) then (C) then (D).

13. A method according to claim 1 in which steps (A) and (C) precede step (B).

14. A method according to claim 13 wherein said solvent is selected from among the group consisting of chlorinated aliphatic hydrocarbons and substituted aromatic hydrocarbons.

15. A method according to claim 13 wherein said phase transfer catalyst is selected from among the group consisting of quaternary ammonium salts, guanidinum salts, pyridinium salts, and phosphonium salts.

16. A method according to claim 15 wherein the amount of said phase transfer catalyst employed is in a range between 0 and about 5 mole percent based on the total number of moles of bisphenol employed.

17. A method according to claim 13 wherein said chain stopper is at least on monofunctional phenol having structure IV wherein $R^{13}$–$R^{17}$ are independently hydrogen, halogen, $C_1$-$C_{20}$ alkyl, $C_6$-$C_{20}$ aryl, $C_7$-$C_{21}$

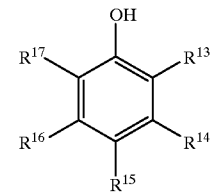

IV aralkyl or $C_5$-$C_{20}$ cycloalkyl groups.

18. A method according to claim 17 wherein the amount of said chain stopper employed is in a range between 0 and about 40 mole percent based on the total number of moles of bisphenol employed.

19. A method according to claim 17 wherein said chain stopper is selected from the group consisting of phenol, p-cumylphenol, mesitol, 2,6-xylenol; 2,4-xylenol; 2,5-xylenol; 2,3,5-xylenol; 2,3,6-xylenol; 2,4,6-triethylphenol; 2,4-di-t-butylphenol; 3,5-di-t-butylphenol; 2,6-dimethyl-4-nonylphenol; 2,6-dibromophenol; 2,5-dibromophenol; 2,6-dichlorophenol; 2,5-dichlorophenol; 4-chloro-2,6-dibromophenol; 4-bromo-2,6-dichlorophenol; 2,4,6-tribromophenol; 2,3,6-tribromophenol; 2,4,6-trichlorophenol; 2,3,6-trichlorophenol; 2,6-dimethyl-4-bromophenol; 4-t-butyl-2,6-dimethylphenol; 2,6-di-t-butyl-4-methylphenol; 3-t-butyl-2,6-dimethyl phenol; 2,6-diphenylphenol; 2-phenylphenol; 2-methyl-6-phenylphenol; 2-methyl-4-phenylphenol; and 2,6-dimethyl-4-phenylphenol.

20. A method according to claim 13 wherein said phase transfer catalyst comprises cations selected from the group consisting of quaternary ammonium cations V

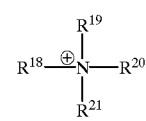

V wherein $R^{18}$–$R^{21}$ are independently $C_1$-$C_{20}$ alkyl, $C_6$-$C_{20}$ aryl, $C_7$-$C_{21}$ aralkyl or $C_5$-$C_{20}$ cycloalkyl, and further $R^{18}$ and $R^{19}$ may together form a $C_4$-$C_{20}$ cycloaliphatic ring which may be substituted by one or more $C_1$-$C_{20}$ alkyl, $C_6$-$C_{20}$ aryl, $C_5$-$C_{21}$ aralkyl, $C_5$-$C_{20}$ cycloalkyl groups or a combination thereof;

guanidinium cations VI

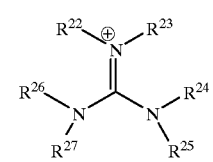

VI wherein $R^{22}$–$R^{27}$ are independently $C_1$-$C_{21}$ alkyl, $C_6$-$C_{20}$ aryl, $C_7$-$C_{21}$, aralkyl or $C_5$-$C_{20}$ cycloalkyl;

pyridinium cations VII

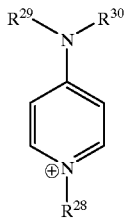

wherein $R^{28}$–$R^{30}$ are independently $C_1$-$C_{20}$ alkyl, $C_6$-$C_{20}$ aryl, $C_7$-$C_{21}$ aralkyl or $C_5$-$C_{20}$ cycloalkyl, and further $R^{29}$ and $R^{30}$ may together form a $C_4$-$C_{20}$ cycloaliphatic ring which may be substituted by one or more $C_1$-$C_{20}$ alkyl, $C_6$-$C_{20}$ aryl, $C_5$-$C_{21}$ aralkyl, $C_5$-$C_{20}$ cycloalkyl groups or a combination thereof, and dialkylaminoquaternary ammonium salts VIII

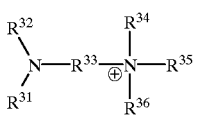

wherein each of $R^{31}$, $R^{32}$, $R^{34}$, $R^{35}$, and $R^{36}$ are $C_1$–$C_{20}$ aliphatic radicals, wherein said radicals $R^{31}$ and $R^{32}$ may together form a cycloaliphatic radical, said radicals $R^{34}$ and $R^{35}$ may together for a cycloaliphatic radical, $R^{33}$ is a $C_2$–$C_{20}$ aliphatic, a $C_5$–$C_{20}$ cycloaliphatic radical or a $C_4$–$C_{20}$ aromatic radical.

21. A method according to claim 13 wherein said bisphenols are selected from the group consisting of 2,2-bis(4-hydroxyphenyl)propane (bisphenol A); 2,2-bis(3-chloro-4-hydroxyphenyl)propane; 2,2-bis(3-bromo-4-hydroxyphenyl)propane; 2,2-bis(4-hydroxy-3-methylphenyl)propane; 2,2-bis(4-hydroxy-3-isopropylphenyl)propane; 2,2-bis(3-t-butyl-4-hydroxyphenyl)propane; 2,2-bis(3-phenyl-4-hydroxyphenyl)propane; 2,2-bis(3,5-dichloro-4-hydroxyphenyl)propane; 2,2-bis(3,5-dibromo-4-hydroxyphenyl)propane; 2,2-bis(3,5-dimethyl-4-hydroxyphenyl)propane; 2,2-bis(3-chloro-4-hydroxy-5-methylphenyl)propane; 2,2-bis(3-bromo-4-hydroxy-5-methylphenyl)propane; 2,2-bis(3-chloro-4-hydroxy-5-isopropylphenyl)propane; 2,2-bis(3-bromo-4-hydroxy-5-isopropylphenyl)propane; 2,2-bis(3-t-butyl-5-chloro-4-hydroxyphenyl)propane; 2,2-bis(3-bromo-5-t-butyl-4-hydroxyphenyl)propane; 2,2-bis(3-chloro-5-phenyl-4-hydroxyphenyl)propane; 2,2-bis(3-bromo-5-phenyl-4-hydroxyphenyl)propane; 2,2-bis(3,5-diisopropyl-4-hydroxyphenyl)propane; 2,2-bis(3,5-di-t-butyl-4-hydroxyphenyl)propane; 2,2-bis(3,5-diphenyl-4-hydroxyphenyl)propane; 2,2-bis(4-hydroxy-2,3,5,6-tetrachlorophenyl)propane; 2,2-bis(4-hydroxy-2,3,5,6-tetrabromophenyl)propane; 2,2-bis(4-hydroxy-2,3,5,6-tetramethylphenyl)propane; 2,2-bis(2,6-dichloro-3,5-dimethyl-4-hydroxyphenyl)propane; 2,2-bis(2,6-dibromo-3,5-dimethyl-4-hydroxyphenyl)propane; 1,1-bis(4-hydroxyphenyl)cyclohexane; 1,1-bis(3-chloro-4-hydroxyphenyl)cyclohexane; 1,1-bis(3-bromo-4-hydroxyphenyl)cyclohexane; 1,1-bis(4-hydroxy-3-methylphenyl)cyclohexane; 1,1-bis(4-hydroxy-3-isopropylphenyl)cyclohexane; 1,1-bis(3-t-butyl-4-hydroxyphenyl)cyclohexane; 1,1-bis(3-phenyl-4-hydroxyphenyl)cyclohexane; 1,1-bis(3,5-dichloro-4-hydroxyphenyl)cyclohexane; 1,1-bis(3,5-dibromo-4-hydroxyphenyl)cyclohexane; 1,1-bis(3,5-dimethyl-4-hydroxyphenyl)cyclohexane; 1,1-bis(3-chloro-4-hydroxy-5-methylphenyl)cyclohexane; 1,1-bis(3-bromo-4-hydroxy-5-methylphenyl)cyclohexane; 1,1-bis(3-chloro-4-hydroxy-5-isopropylphenyl)cyclohexane; 1,1-bis(3-bromo-4-hydroxy-5-isopropylphenyl)cyclohexane; 1,1-bis(3-t-butyl-5-chloro-4-hydroxyphenyl)cyclohexane; 1,1-bis(3-bromo-5-t-butyl-4-hydroxyphenyl)cyclohexane; 1,1-bis(3-chloro-5-phenyl-4-hydroxyphenyl)cyclohexane; 1,1-bis(3-bromo-5-phenyl-diisopropyl-4-hydroxyphenyl)-cyclohexane; 1,1-bis(3,5-diisopropyl-4-hydroxyphenyl)cyclohexane; 1,1-bis(3,5-di-t-butyl-4-hydroxyphenyl)cyclohexane; 1,1-bis(3,5-diphenyl-4-hydroxyphenyl)cyclohexane; 1,1-bis(4-hydroxy-2,3,5,6-tetrachlorophenyl)cyclohexane; 1,1-bis(4-hydroxy-2,3,5,6-tetrabromophenyl)cyclohexane; 1,1-bis(4-hydroxy-2,3,5,6-tetramethylphenyl)cyclohexane; 1,1-bis(2,6-dichloro-3,5-dimethyl-4-hydroxyphenyl)cyclohexane; 1,1-bis(2,6-dibromo-3,5-dimethyl-4-hydroxyphenyl)cyclohexane; 1,1-bis(4-hydroxyphenyl)-3,3,5-trimethylcyclohexane; 1,1-bis(3-chloro-4-hydroxyphenyl)-3,3,5-trimethylcyclohexane; 1,1-bis(3-bromo-4-hydroxyphenyl)-3,3,5-trimethylcyclohexane; 1,1-bis(4-hydroxy-3-methylphenyl)-3,3,5-trimethylcyclohexane; 1,1-bis(4-hydroxy-3-isopropylphenyl)-3,3,5-trimethylcyclohexane; 1,1-bis(3-t-butyl-4-hydroxyphenyl)-3,3,5-trimethylcyclohexane; 1,1-bis(3-phenyl-4-hydroxyphenyl)-3,3,5-trimethylcyclohexane; 1,1-bis(3,5-dichloro-4-hydroxyphenyl)-3,3,5-trimethylcyclohexane; 1,1-bis(3,5-dibromo-4-hydroxyphenyl)-3,3,5-trimethylcyclohexane; 1,1-bis(3,5-dimethyl-4-hydroxyphenyl)-3,3,5-trimethylcyclohexane; 1,1-bis(3-chloro-4-hydroxy-5-methylphenyl)-3,3,5-trimethylcyclohexane; 1,1-bis(3-bromo-4-hydroxy-5-methylphenyl)-3,3,5-trimethyl-3,3,5-trimethylcyclohexane; 1,1-bis(3-chloro-4-hydroxy-5-isopropylphenyl)-3,3,5-trimethylcyclohexane; 1,1-bis(3-bromo-4-hydroxy-5-isopropylphenyl)-3,3,5-trimethylcyclohexane; 1,1-bis(3-t-butyl-5-chloro-4-hydroxyphenyl)-3,3,5-trimethylcyclohexane; 1,1-bis(3-bromo-5-t-butyl-4-hydroxyphenyl)-3,3,5-trimethylcyclohexane; 1,1-bis(3-chloro-5-phenyl-4-hydroxyphenyl)-3,3,5-trimethylcyclohexane; 1,1-bis(3-bromo-5-phenyl-4-hydroxyphenyl)-3,3,5-trimethylcyclohexane; 1,1-bis(3,5-diisopropyl-4-hydroxyphenyl)-3,3,5-trimethylcyclohexane; 1,1-bis(3,5-di-t-butyl-4-hydroxyphenyl)-3,3,5-trimethylcyclohexane; 1,1-bis(3,5-diphenyl-4-hydroxyphenyl)-3,3,5-trimethylcyclohexane; 1,1-bis(4-hydroxy-2,3,5,6-tetrachlorophenyl)-3,3,5-trimethylcyclohexane; 1,1-bis(4-hydroxy-2,3,5,6-tetrabromophenyl)-3,3,5-trimethylcyclohexane; 1,1-bis(4-hydroxy-2,3,5,6-tetramethylphenyl)-3,3,5-trimethylcyclohexane; 1,1-bis(2,6-dichloro-3,5-dimethyl-4-hydroxyphenyl)-3,3,5-trimethylcyclohexane; 1,1-bis(2,6-dibromo-3,5-dimethyl-4-hydroxyphenyl)-3,3,5-trimethylcyclohexane; 4,4'dihydroxy-3,5,3',5'-tetrabromo-1,1-biphenyl; 4,4'-dihydroxy-3,5,3',5'-tetramethyl-1,1-biphenyl; 4,4'-dihydroxy-3,3'-dimethyl-1,1-biphenyl; 4,4'-dihydroxy-3,5-dimethyldiphenylether; 4,4'-dihydroxy-3,5,3',5'-tetrabromodiphenylether; 4,4'-dihydroxy-3,5,3',5'-tetramethyldiphenylthioether; 1,3-bis(2-(3,5-dimethyl-4-hydroxyphenyl)-2-propyl)benzene and 1,3-bis(2-(3,5-dibromo-4-hydroxyphenyl)-2-propyl)benzene.

22. A method according to claim 13 wherein said solvent is methylene chloride.

23. A method according to claim 13 wherein the polycarbonate comprising structural units I has a weight average molecular weight of between about 500 and about 200,000 daltons.

24. A method for making a polycarbonate comprising structural units IX

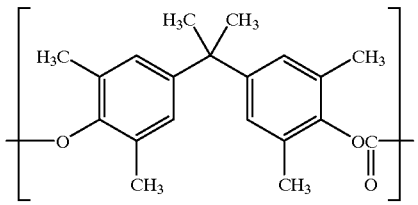

said method comprising:
(A) admixing 1 molar equivalent of 2,2-bis(3,5-dimethyl-4-hydroxyphenyl)propane with 0 to 0.25 molar equivalents of a chainstopper, methylene chloride, water, and 0 to 0.05 molar equivalents of a phase transfer catalyst;
(B) adding phosgene and sufficient aqueous base to maintain a pH in a range between about 11 and about 14 to the mixture formed in step (A); said phosgene being added incrementally in an amount equivalent to between about 1.01 to about 1.3 equivalents based upon the amount of bisphenol used in step (A);
(C) adding an amine catalyst in an amount corresponding to between about 0.001 and about 0.04 equivalents based upon the amount of bisphenol used in step (A), said catalyst being selected from the group consisting of N,N-dimethylethylamine, N,N-dimethylpropylamine, N,N-dimethylbutylamine, N,N-dimethylpentylamine, N,N-dimethylhexylamine, N,N-dimethylheptylamine, N,N-dimethyloctylamine, N,N-dimethylnonylamine, N,N-dimethyldecylamine, N,N-dimethyldodecylamine, N,N-dimethylhexadecylamine, N,N-dimethyloctadecylamine; and
(D) agitating the mixture formed by steps (A), (B) and (C) at a pH in a range between about 8 and about 13 until said mixture is free of chloroformate groups.

25. A method according to claim 24 in which the chain stopper is selected from the group consisting of phenol, p-cumylphenol, mesitol, 2,6-xylenol; 2,4-xylenol; 2,5-xylenol; 2,3,5-xylenol; 2,3,6-xylenol; 2,4,6-triethylphenol; 2,4-di-t-butylphenol; 3,5-di-t-butylphenol; 2,6-dimethyl-4-nonylphenol; 2,6-dibromophenol; 2,5-dibromophenol; 2,6-dichlorophenol; 2,5-dichlorophenol; 4-chloro-2,6-dibromophenol; 4-bromo-2,6-dichlorophenol; 2,4,6-tribromophenol; 2,3,6-tribromophenol; 2,4,6-trichlorophenol; 2,3,6-trichlorophenol; 2,6-dimethyl-4-bromophenol; 4-t-butyl-2,6-dimethylphenol; 2,6-di-t-butyl-4-methylphenol; 3-t-butyl-2,6-dimethyl phenol; 2,6-diphenylphenol; 2-phenylphenol; 2-methyl-6-phenylphenol; 2-methyl-4-phenylphenol; and 2,6-dimethyl-4-phenylphenol.

26. A method according to claim 24 wherein the phase transfer catalyst is selected from the group consisting of tetraalkylammonium halides, hexaalkylguanidium halides, N-alkylpyridinium halides, N-aralkylpyridinium halides dialkylamino quaternary ammonium halides, tetraalkylphosphonium halides, tetraalkylphosphonium hydroxides, alkyltriarylphosphonium halides and alkyltriarylphosphonium hydroxides.

27. A method according to claim 24 wherein the order of the steps is (A) then (B) then (C) then (D).

28. A method according to claim 24 wherein steps (A) and (C) precede step (B).

29. A process for making a polycarbonate comprising structural units X

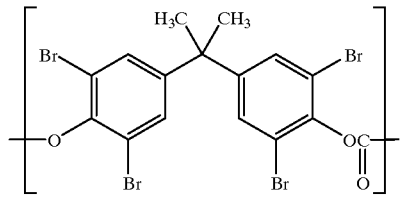

said method comprising:
(A) admixing 1 molar equivalent of 2,2-bis(3,5-dibromo-4-hydroxyphenyl)propane with 0 to 0.25 molar equivalents of a chainstopper, methylene chloride, water, and 0 to 0.05 molar equivalents of a phase transfer catalyst;
(B) adding phosgene and sufficient aqueous base to maintain a pH in a range between about 11 and about 14 to the mixture formed in step (A); said phosgene being added incrementally in an amount equivalent to between about 1.01 to about 1.3 equivalents based upon the amount of bisphenol used in step (A);
(C) adding an amine catalyst in an amount corresponding to between about 0.001 and about 0.04 equivalents based upon the amount of bisphenol used in step (A), said catalyst being selected from the group consisting of N,N-dimethylethylamine, N,N-dimethylpropylamine, N,N-dimethylbutylamine, N,N-dimethylpentylamine, N,N-dimethylhexylamine, N,N-dimethylheptylamine, N,N-dimethyloctylamine, N,N-dimethylnonylamine, N,N-dimethyldecylamine, N,N-dimethyldodecylamine, N,N-dimethylhexadecylamine, N,N-dimethyloctadecylamine; and
(D) agitating the mixture formed by steps (A), (B) and (C) at a pH in a range between about 8 and about 13 until said mixture is free of chloroformate groups.

30. A method according to claim 29 in which the chain stopper is selected from the group consisting of phenol, p-cumylphenol, mesitol, 2,6-xylenol; 2,4-xylenol; 2,5-xylenol; 2,3,5-xylenol; 2,3,6-xylenol; 2,4,6-triethylphenol; 2,4-di-t-butylphenol; 3,5-di-t-butylphenol; 2,6-dimethyl-4-nonylphenol; 2,6-dibromophenol; 2,5-dibromophenol; 2,6-dichlorophenol; 2,5-dichlorophenol; 4-chloro-2,6-dibromophenol; 4-bromo-2,6-dichlorophenol; 2,4,6-tribromophenol; 2,3,6-tribromophenol; 2,4,6-trichlorophenol; 2,3,6-trichlorophenol; 2,6-dimethyl-4-bromophenol; 4-t-butyl-2,6-dimethylphenol; 2,6-di-t-butyl-4-methylphenol; 3-t-butyl-2,6-dimethyl phenol; 2,6-diphenylphenol; 2-phenylphenol; 2-methyl-6-phenylphenol; 2-methyl-4-phenylphenol; and 2,6-dimethyl-4-phenylphenol.

31. A method according to claim 29 wherein the phase transfer catalyst is selected from the group consisting of tetraalkylammonium halides, hexaalkylguanidium halides, N-alkylpyridinium halides, N-aralkylpyridinium halides dialkylamino quaternary ammonium halides, tetraalkylphosphonium halides, tetraalkylphosphonium hydroxides, alkyltriarylphosphonium halides and alkyltriarylphosphonium hydroxides.

32. A method according to claim 29 wherein the order of the is (A) then (B) then (C) then (D).

33. A method according to claim 29 wherein steps (A) and (C) precede step (B).

34. A polycarbonate composition prepared by the method of claim 1 in which from about 90 to 100 percent of the repeat units have structure IX

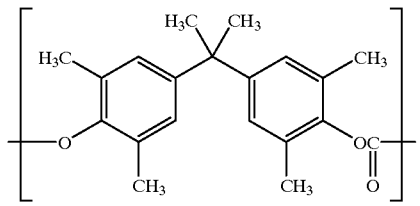

IX said polycarbonate having a weight average molecular weight of between about 40,000 and about 175,000 daltons.

35. A molded article comprising the polycarbonate according to claim 34.

36. A polycarbonate composition prepared by the method of claim 1 in which from about 90 to 100 percent of the repeat units have structure X

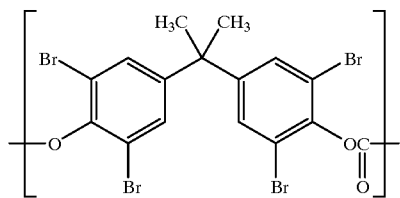

X said polycarbonate having a weight average molecular weight of between about 40,000 and about 175,000 daltons.

37. A molded article comprising the polycarbonate according to claim 36.

38. A method of preparing symmetrical hindered diaryl carbonates having structure XI

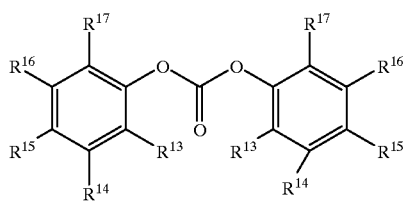

XI wherein $R^{13}$–$R^{17}$ are independently hydrogen, halogen, $C_1$-$C_{20}$ alkyl, $C_6$-$C_{20}$ aryl, $C_7$-$C_{21}$ aralkyl or $C_5$-$C_{20}$ cycloalkyl groups;

said method comprising:
(A') admixing at least one solvent, water, and optionally one or more phase transfer catalysts, with at least one phenol having structure IV

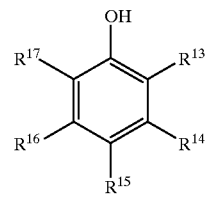

IV (B') adding phosgene and sufficient aqueous base to maintain a pH in a range between about 5 and about 8.5; said phosgene being added incrementally in an amount equivalent to between about 1.01 to about 1.2 equivalents based upon the amount of phenol used in step (A');

(C') adding from about 1 to about 1.05 molar equivalents relative to the amount of phenol used in step (A') of aqueous base and a catalyst in an amount corresponding to between about 0.001 and about 0.10 molar equivalents based upon the amount of phenol used in step (A'), said catalyst

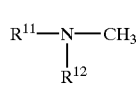

III being selected from the group consisting of N,N-dimethylethylamine, N,N-dimethylpropylamine, N,N-dimethylbutylamine, N,N- dimethylpentylamine, N,N-dimethylhexylamine, N,N-dimethylheptylamine, N,N-dimethyloctylamine, N,N-dimethylnonylamine, N,N-dimethyldecylamine, N,N-dimethyldodecylamine, N,N-dimethylhexadecylamine, N,N-dimethyloctadecylamine; and (D') agitating the mixture formed by steps (A'), (B') and (C') at a pH in a range between about 8 and about 13 until said mixture is free of chloroformate groups.

39. A method according to claim 40 in which said phenol IV is selected from the group consisting of mesitol, 2,6-xylenol; 2,4-xylenol; 2,5-xylenol; 2,3,5-xylenol; 2,3,6-xylenol; 2,4,6-triethylphenol; 2,4-di-t-butylphenol; 3,5-di-t-butylphenol; 2,6-dimethyl-4-nonylphenol; 2,6-dibromophenol; 2,5-dibromophenol; 2,6-dichlorophenol; 2,5-dichlorophenol; 4-chloro-2,6-dibromophenol; 4-bromo-2,6-dichlorophenol; 2,4,6-tribromophenol; 2,3,6-tribromophenol; 2,4,6-trichlorophenol; 2,3,6-trichlorophenol; 2,6-dimethyl-4-bromophenol; 4-t-butyl-2, 6-dimethylphenol; 2,6-di-t-butyl-4-methylphenol; 3-t-butyl-2,6-dimethyl phenol; 2,6-diphenylphenol; 2-phenylphenol; 2-methyl-6-phenylphenol; 2-methyl-4-phenylphenol; and 2,6-dimethyl-4-phenylphenol.

40. A method according to claim 38 in which said phase transfer catalyst is selected from the group consisting of tetraalkylammonium halides, hexaalkylguanidium halides, N-alkylpyridinium halides, N-aralkylpyridinium halides dialkylamino quaternary ammonium halides, tetraalkylphosphonium halides, tetraalkylphosphonium hydroxides, alkyltriarylphosphonium halides and alkyltriarylphosphonium hydroxides.

41. A method according to claim 38 wherein said solvent is methylene chloride.

42. A method according to claim 38 wherein the order of the steps is (A') then (B') then (C') then (D').

43. A method according to claim 38 wherein steps (A') and (C') precede step (B').

44. A method of preparing 2,4,6-tribromophenyl carbonate, said method comprising:

(A') admixing methylene chloride, water and 2,4,6-tribromophenol;

(B') adding phosgene and sufficient aqueous base to maintain a pH in a range between about 5 and about 8.5; said phosgene being added incrementally in an amount equivalent to between about 1.01 to about 1.5 equivalents based upon the amount of 2,4,6-tribromophenol used in step (A');

(C') adding from about 3 to about 4 molar equivalents of aqueous base relative to the amount of 2,4,6-tribromophenol used in step (A') and N,N-dimethylbutylamine in an amount corresponding to between about 0.001 and about 0.10 molar equivalents based upon the amount of 2,4,6-tribromophenol used in step (A'); and (D') agitating the mixture formed by steps (A'), (B') and (C') at a pH in a range between about 8 and about 13 until said mixture is free of chloroformate groups.

* * * * *